United States Patent
Asahi et al.

(10) Patent No.: US 9,237,901 B2
(45) Date of Patent: Jan. 19, 2016

(54) LIQUID INJECTION DEVICE AND MEDICAL APPARATUS

(75) Inventors: Tsunemori Asahi, Azumino (JP); Hirokazu Sekino, Chino (JP)

(73) Assignee: Seiko Epson Corporation, Tokyo (JP)

( * ) Notice: Subject to any disclaimer, the term of this patent is extended or adjusted under 35 U.S.C. 154(b) by 615 days.

(21) Appl. No.: 13/616,884

(22) Filed: Sep. 14, 2012

(65) Prior Publication Data

US 2013/0096601 A1 Apr. 18, 2013

(30) Foreign Application Priority Data

Oct. 17, 2011 (JP) .................................. 2011-227662

(51) Int. Cl.
*A61B 17/3203* (2006.01)
*A61B 17/00* (2006.01)
*A61B 19/00* (2006.01)

(52) U.S. Cl.
CPC ... *A61B 17/3203* (2013.01); *A61B 2017/00482* (2013.01); *A61B 2019/4815* (2013.01)

(58) Field of Classification Search
CPC ................ A61B 17/3203; A61B 2017/00154; A61B 10/02; A61B 2019/4815; A61B 2017/00482; B41J 2/19; B41J 2/17596; B05B 1/086; B05B 17/0607; B65D 83/00
USPC .......... 83/177, 100; 606/190, 167, 79, 83, 13, 606/159, 166, 170, 48, 131, 890.1; 604/27, 604/28, 25, 43, 146, 150, 289, 310, 311, 67, 604/65, 118, 151, 246, 121, 152; 239/2.1, 239/101, 102.2, 589.1
See application file for complete search history.

(56) References Cited

U.S. PATENT DOCUMENTS

| | | | |
|---|---|---|---|
| 6,370,411 B1 | 4/2002 | Osadchy et al. | |
| 6,645,149 B1 | 11/2003 | Smith | |
| 7,901,374 B2 * | 3/2011 | Seto et al. | 604/48 |
| 8,308,745 B2 * | 11/2012 | Seto et al. | 606/167 |
| 8,382,702 B2 * | 2/2013 | Uchida et al. | 604/67 |
| 2009/0043480 A1* | 2/2009 | Seto et al. | 701/103 |
| 2011/0009812 A1* | 1/2011 | Brown | 604/31 |
| 2014/0243787 A1* | 8/2014 | Mukai et al. | 604/506 |

FOREIGN PATENT DOCUMENTS

| | | |
|---|---|---|
| JP | 2001-520565 | 10/2001 |
| JP | 2002-540880 | 12/2002 |
| JP | 2006-507033 | 3/2006 |
| JP | 2008-082202 | 4/2008 |
| JP | 2010-082305 | 4/2010 |
| WO | 99/40856 | 8/1999 |
| WO | 00/61006 | 10/2000 |
| WO | 2004/009014 | 1/2004 |

* cited by examiner

*Primary Examiner* — Ghassem Alie
(74) *Attorney, Agent, or Firm* — Workman Nydegger (57) ABSTRACT

A liquid injection device includes an injection unit which injects a liquid, a liquid supply instrument which supplies the liquid to the injection unit, and a control unit which controls operation of the injection unit and the liquid supply instrument, wherein the injection unit includes a distal end portion where a nozzle for injecting the liquid is formed, and a body portion in which the distal end portion is removably loaded, at the distal end portion, a distal end-side memory is provided in which first startup data is written, and the control unit is a control unit which reads and writes the first startup data from and to the distal end-side memory in the distal end portion loaded in the body portion and manages use time of the distal end portion based on the first startup data that is read out.

10 Claims, 11 Drawing Sheets

| YEAR/MONTH/DAY/HOUR/MINUTE | DRIVE TIME | NUMBER OF TIMES OF DRIVING | DRIVE VOLTAGE | DRIVE FREQUENCY |
|---|---|---|---|---|
| yr1/mt1/da1/hr1/mn1 | T1 | N1 | V1 | C1 |
| yr1/mt1/da2/hr2/mn2 | T2 | N2 | V2 | C2 |
| yr1/mt1/da3/hr3/mn3 | T3 | N3 | V3 | C3 |
|  |  |  |  |  |
|  |  |  |  |  |
|  |  |  |  |  |
|  |  |  |  |  |

| YEAR/MONTH/DAY/HOUR/MINUTE |
|---|
| yr1/mt1/da1/hr1/mn1 |
| yr1/mt1/da2/hr2/mn2 |
| yr1/mt1/da3/hr3/mn3 |
| |
| |
| |
| |
| |

FIG.10

| FIRST STARTUP DATE AND TIME | yr1/mt1/da1/hr1/mn1 |
|---|---|
| NUMBER OF TIMES OF PAST STARTUP | 2 |

LIQUID INJECTION DEVICE AND MEDICAL APPARATUS

BACKGROUND

1. Technical Field

The present invention relates to a liquid injection device which injects a liquid from a nozzle to incise or excise a living tissue.

2. Related Art

A liquid injection device which injects a liquid such as water or physiological saline solution toward a living tissue and thus incises or excises the living tissue is developed. In a surgical operation using such a liquid injection device, only a tissue of an internal organ or the like can be selectively incised or excised without damaging nerves and blood vessels. Therefore, the burden on the patient can be reduced.

Also, a liquid injection device which injects a liquid in a pulsed manner instead of continuously injecting a liquid from a nozzle and thus can incise or excise a living tissue with a small amount of injection is proposed (JP-A-2008-82202). In this liquid injection device, a liquid is supplied to a liquid chamber using a supply pump and the volume of the liquid chamber is reduced to pressurize the liquid, thus injecting the liquid from a nozzle in a pulsed manner.

These liquid injection devices have an injection unit (hereinafter referred to as an applicator) in which a nozzle for injecting the liquid is formed and which an operator holds in his or her hand to operate, a supply pump for supplying the liquid to the applicator, a connection tube connecting the supply pump with the applicator, and the like. Also, a liquid chamber connected to the nozzle, an actuator which deforms the liquid chamber to reduce the volume of the liquid chamber, and the like are provided within the applicator of the liquid injection device which injects the liquid in a pulsed manner.

However, such a liquid injection device has the following problem. That is, in the applicator, the inside liquid contacts the outside air at the part of the nozzle. Therefore, if the absence of injection of the liquid continues, the outside air may enter the inside of the applicator from the part of the nozzle. Consequently, there is a problem that various bacteria can propagate within the applicator over a long period of time.

SUMMARY

An advantage of some aspects of the invention is that for a liquid injection device which injects a liquid from a nozzle of an applicator, a technique which can prevent propagation of various bacteria within the applicator can be provided.

An aspect of the invention is directed to a liquid injection device including an injection unit which injects a liquid, a fluid supply instrument which supplies the liquid to the injection unit, and a control unit which controls operation of the injection unit and the liquid supply instrument. The injection unit includes a distal end portion where a nozzle for injecting the liquid is formed, and a body portion in which the distal end portion is removably loaded. At the distal end portion, a distal end-side memory is provided in which first startup data, which is data related to date and time when the liquid injection device is started up for the first time as the distal end portion is loaded in the body portion, is written. The control unit is a control unit which reads and writes the first startup data from and to the distal end-side memory in the distal end portion loaded in the body portion and manages use time of the distal end portion based on the first startup data that is read out.

In the liquid injection device according to this aspect, the injection unit which injects the liquid is divided into the distal end portion and the body portion. The nozzle is formed at the distal end portion and the distal end portion is removably provided in the body portion. Also, the memory (distal end-side memory) is loaded in the distal end portion. In this memory, data (first startup data) about the date and time when the operator (user) of the liquid injection device starts up, for the first time, the liquid injection device with the distal end portion loaded in the body portion, is written. The first startup data is sufficient if the first startup data can specify the date and time when the liquid injection device is started up for the first time as the distal end portion is loaded in the body portion, and the first startup data does not necessarily have to be data of the very date and time. For example, if the time elapsed since the liquid injection device is started up for the first time as the distal end portion is loaded in the body portion is known, the date and time when the liquid injection device is started up for the first time can be specified by retrospectively tracing back from the current date and time. Therefore, the time elapsed can be used as the first startup data. The control unit of the liquid injection device reads and writes the first startup data from and to the distal end-side memory of the distal end portion loaded in the body portion, and manages the use time of the distal end portion based on the first startup data that is read out. For example, if the distal end portion is left attached to the body portion over a long period of time, the operator of the liquid injection device can be notified to that effect. As a form of notification, the date and time when the distal end portion is used for the first time after being loaded in the body portion can be displayed, thus notifying the operator that there is already a lapse of a long time since the start of the use of the distal end portion. Alternatively, the time elapsed since the use of the distal end portion is started may be displayed. Moreover, a sound such as a buzz may be outputted, or a lamp may be switched on or flashed. Of course, if the distal end portion is left attached to the body portion over an excessively long time, measures for not only notifying the operator to that effect but also restraining the startup of the liquid injection device may be taken.

Thus, the distal end portion is replaced before being left attached over a long period of time, and therefore growth of various bacteria inside is prevented. A distal end-side memory is also loaded in the newly arranged distal end portion. Therefore, the control unit of the liquid injection device can manage the use time of the distal end portion by writing first startup data into the distal end-side memory when the liquid injection device is started up for the first time as this distal end portion is loaded.

In the liquid injection device according to the above aspect, number of times of startup data (data related to the number of times the liquid injection device is started up as the distal end portion is loaded) may be written in the distal end-side memory, in addition to the first startup data. The number of times of startup data may be data related to the number of times the liquid injection device is started up as the distal end portion is loaded, and the number of times of startup data does not necessarily have to be data indicating the very number of times. For example, by adding the date and time when the liquid injection device is started up as the distal end portion is loaded (startup date and time), the number of times of startup can be specified based on the number of startup dates and times stored in the distal end-side memory. Of course, the number of times of startup stored in the distal end-side memory may be updated every time the liquid injection device is started up. The control unit of the liquid injection device may manage the use time of the distal end portion based on the first startup data and the number of times of startup data read out from the distal end-side memory.

It can be considered that the fact that the liquid injection device is started up several times in the state where the distal end portion is loaded in the body portion instrument that the distal end portion is reused. As the distal end portion is reused, there is a greater risk of growth of various bacteria inside, than in the case where the distal end portion is used continuously. Therefore, by storing not only the first startup data but also the number of times of startup data in the distal end-side memory and managing the use time of the distal end portion based on these data, it is possible to avoid the growth of various bacteria within the distal end portion more securely.

The liquid injection device according to the above aspect may be configured as follows. First, a liquid chamber to which the liquid is supplied from the liquid supply instrument and which is connected to the nozzle may be provided in the distal end portion. Also, a piezoelectric element which deforms according to a voltage of an applied drive signal and changes a volume of the liquid chamber may be provided in the body portion. Then, by applying the drive signal to the piezoelectric element to reduce the volume of the liquid chamber in the state where the liquid is supplied to the liquid chamber from the liquid supply instrument, the liquid may be injected from the nozzle in a pulsed manner. A memory (body-side memory) may be loaded in the body portion of the liquid injection device configured in this manner, and data (drive time data) related to a drive time during which the drive signal is applied to the piezoelectric element may be stored in the body-side memory. The drive time data may be data in which a finalized drive time is additionally stored every time the liquid injection device is stopped and thus the drive time is finalized (data indicating the drive time for every startup), or may be data in which a cumulative value of these drive times is stored. The control unit may manage use time of the body portion based on the drive time data read out from the body-side memory.

Thus, the use time of the body portion can be managed in such a way that the drive time of the piezoelectric element loaded in the body portion does not exceed a predetermined time. Therefore, the body portion of the liquid injection device can be replaced before any trouble occurs in a moving part incorporated in the body portion in order to inject the liquid in a pulsed manner. Of course, since the distal end portion can be replaced before the body portion is replaced, the growth of various bacteria within the distal end portion can be avoided.

In the liquid injection device according to the above aspect which injects the liquid in a pulsed manner, data about the number of times the piezoelectric element is driven (the number of times the drive signal is applied to the piezoelectric element) (number of times of driving data) may be stored in the body-side memory. The number of times of driving data may be data in which the finalized number of times of driving is additionally stored every time the liquid injection device is stopped and thus the number of times of driving is finalized, or may be data in which a cumulative value of these numbers of times of driving is stored. The control unit may manage the use time of the body portion based on the number of times of driving data read out from the body-side memory.

Thus, the use time of the body portion can be managed in such a way that the number of times the piezoelectric element loaded in the body portion is driven does not exceed a predetermined number of times. Therefore, the body portion of the liquid injection device can be replaced before any trouble occurs in a moving part incorporated in the body portion in order to inject the liquid in a pulsed manner. Of course, since the distal end portion can be replaced before the body portion is replaced, the growth of various bacteria within the distal end portion can be avoided.

In the liquid injection device according to the above aspect in which the number of times of driving is stored in the body-side memory, the number of times of driving data related to the number of times the piezoelectric element is driven and the voltage of the drive signal applied to the piezoelectric element may be stored. For example, two types of data, that is, data of the number of times the piezoelectric element is driven and data of the voltage of the drive signal, can be stored as the number of times of driving data. Alternatively, the number of times of driving data may be stored in the form of data of the number of times of driving that is weighted according to the voltage of the drive signal, instead of directly storing the data of the number of times the piezoelectric element is driven.

Thus, the use time of the body portion can be managed in consideration of the amount of deformation of the piezoelectric element (voltage of the drive signal) as well as the number of times the piezoelectric element is driven. Therefore, the occurrence of any trouble in a moving part incorporated in the body portion during the use of the liquid injection device can be avoided more securely.

The liquid injection device according to the above aspect can be utilized for a surgical instrument for incising or excising a living tissue by injecting a liquid to the living tissue. The liquid injection device can also be utilized as a treatment instrument which injecting a medical fluid to a living tissue. Therefore, the liquid injection device according to the above aspect can be suitably applied as a medical apparatus.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, in order to clarify the contents of the invention, an embodiment is described in the following order.

Figure 1:
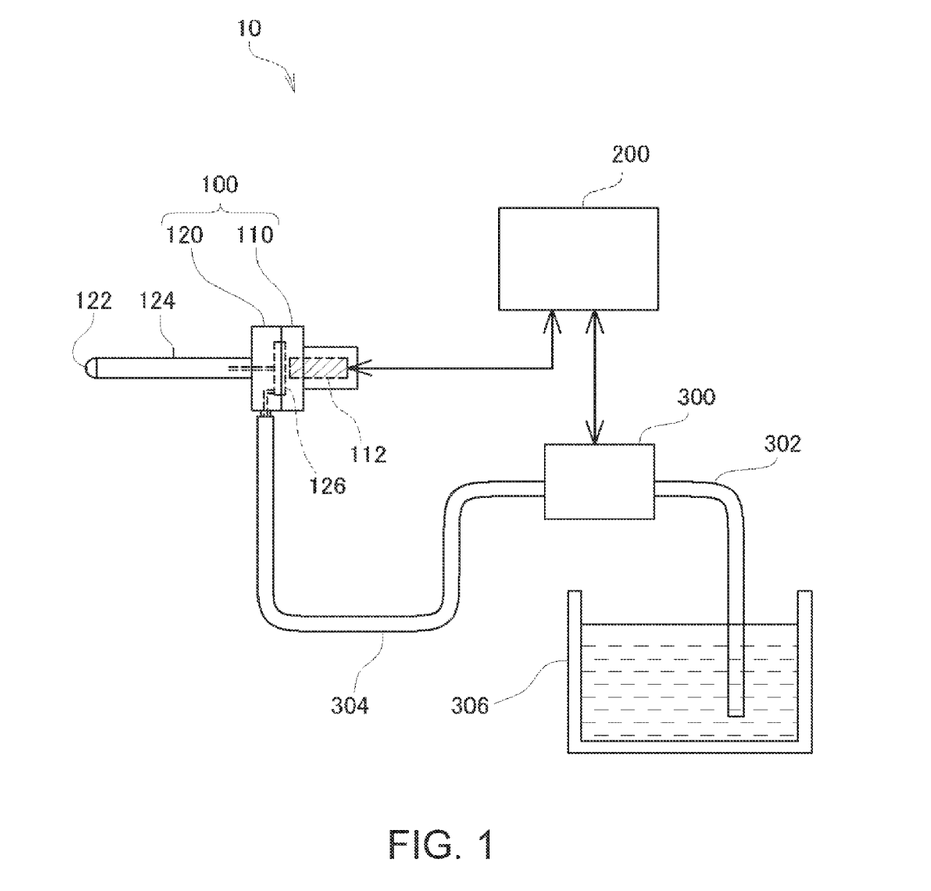
FIG. 1 is an explanatory view showing the schematic configuration of a liquid injection device according to an embodiment.

A. Configuration of Device:
A-1. Configuration of Liquid Injection Device:
A-2. Configuration of Applicator:
A-3. Configuration of Control Unit:
B. Use Time Management Processing:
B-1. Processing on Startup:
B-2. Processing during Operation:
B-3. Processing on Stop:
A. Configuration of Device
A-1. Configuration of Liquid Injection Device FIG. 1 is an explanatory view showing the schematic configuration of a liquid injection device 10 according to this embodiment. The liquid injection device 10 shown in FIG. 1 is used for a surgical technique where a liquid such as water or physiological saline solution is injected toward a living tissue to incise or excise the living tissue.

As shown in FIG. 1, the liquid injection device 10 of this embodiment includes an applicator 100 which an operator holds in his or her hand and operates to inject a liquid, a liquid supply instrument 300 which supplies the liquid to the applicator 100, a liquid container 306 which accommodates the liquid to be injected, a control unit 200 which controls operation of the applicator 100 and the liquid supply instrument 300, and the like. In this embodiment, the applicator 100 is equivalent to the "injection unit" according to the invention.

The applicator 100 roughly includes a body portion 110, a distal end portion 120 removably attached to the body portion 110, and the like. A liquid injection pipe 124 is provided standing in the distal end portion 120. A nozzle 122 is formed at a distal end of the liquid injection pipe 124. Also, a liquid chamber 126 filled with a liquid is provided on the side of the distal end portion 120 that is attached to the body portion 110. This liquid chamber 126 is connected to the nozzle 122 via the liquid injection pipe 124 and is also supplied with a fluid from a second connection tube 304. Moreover, a piezoelectric element 112 formed by a multilayer-type piezoelectric element is provided in the body portion 110. As will be described in detail later, as the distal end portion 120 is attached to the body portion 110 and a drive signal is applied to the piezoelectric element 112, the piezoelectric element 112 expands and contracts, thus changing the volume of the liquid chamber 126. Consequently, the liquid in the liquid chamber 126 is injected in a pulsed manner from the nozzle 122. Although the liquid injection device 10 of this embodiment is described as injecting the liquid in a pulsed manner from the nozzle 122, the liquid injection device may inject the liquid continuously from the nozzle 122. The detailed configuration of the applicator 100 will be described later.

The liquid supply instrument 300 is connected to the liquid container 306 via a first connection tube 302 and supplies the liquid sucked from the liquid container 306 to the liquid chamber 126 of the applicator 100 via the second connection tube 304. The liquid supply instrument 300 of this embodiment is configured in such a way that two pistons slide in cylinders. By properly controlling the moving speed of the two pistons, it is possible to feed the liquid in a pressurized state toward the applicator 100 under a predetermined pressure.

A-2. Configuration of Applicator

Figure 2A:
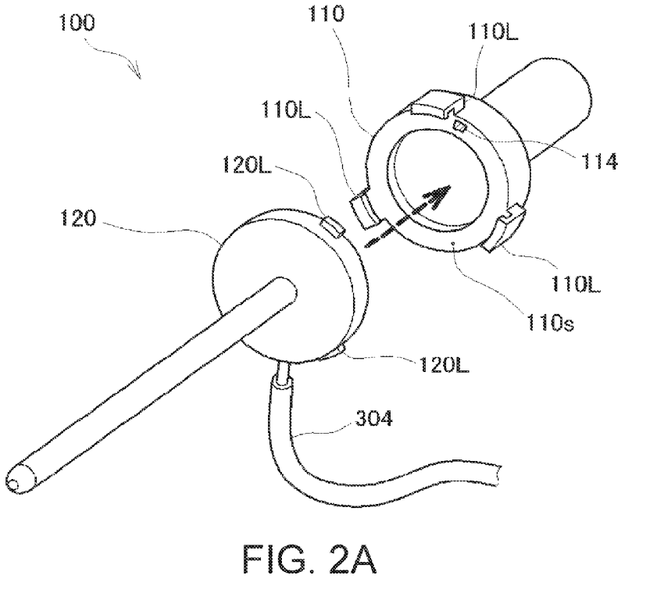
FIGS. 2A and 2B are explanatory views showing the way a distal end portion is attached to a body portion of an applicator.
Figure 2B:
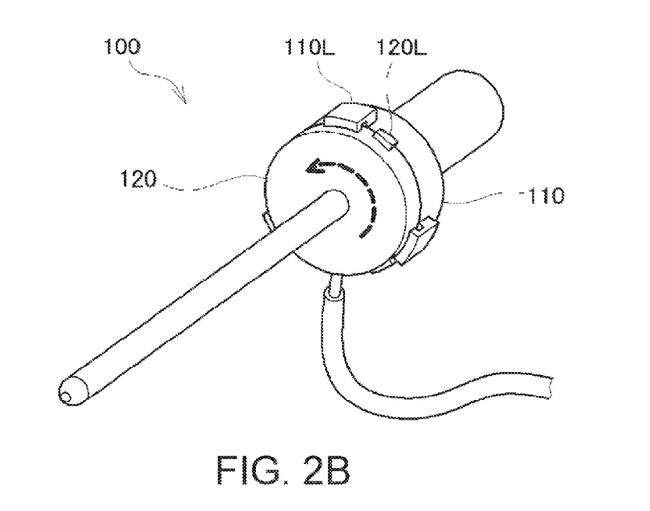

FIGS. 2A and 2B are explanatory views showing the way the distal end portion 120 is attached to the body portion 110 of the applicator 100. As shown in FIG. 2A, plural (in the illustrated example, three) female lock parts 110L are provided at equal intervals on an outer peripheral surface of the body portion 110, and plural (in the illustrated example, three) male lock parts 120L are provided at equal intervals on an outer peripheral surface of the distal end portion 120. To attach the distal end portion 120 to the body portion 110, the distal end portion 120 is made to abut on a joint surface 110s of the body portion 110 in such a way that the male lock parts 120L are not situated at the same positions as the female lock parts 110L. After that, as shown in FIG. 2B, the distal end portion 120 is turned counterclockwise, with the distal end portion 120 kept abutting on the body portion 110. Thus, the male lock parts 120L formed on the distal end portion 120 engage with the female lock parts 110L on the body portion 110, enabling the distal end portion 120 to be firmly attached to the body portion 110. Meanwhile, to detach the distal end portion 120 from the body portion 110, the distal end portion 120 is turned clockwise. Thus, the male lock parts 120L are disengaged from the female lock parts 110L, enabling the distal end portion 120 to be detached from the body portion 110.

In this embodiment, a memory is arranged within the distal end portion 120, as described below. Moreover, a connection terminal 114 is provided on the joint surface 110s of the body portion 110. As the distal end portion 120 is attached to the body portion 110, data in the memory of the distal end portion 120 can be read out or data can be written therein via the connection terminal 114.

Figure 3A:
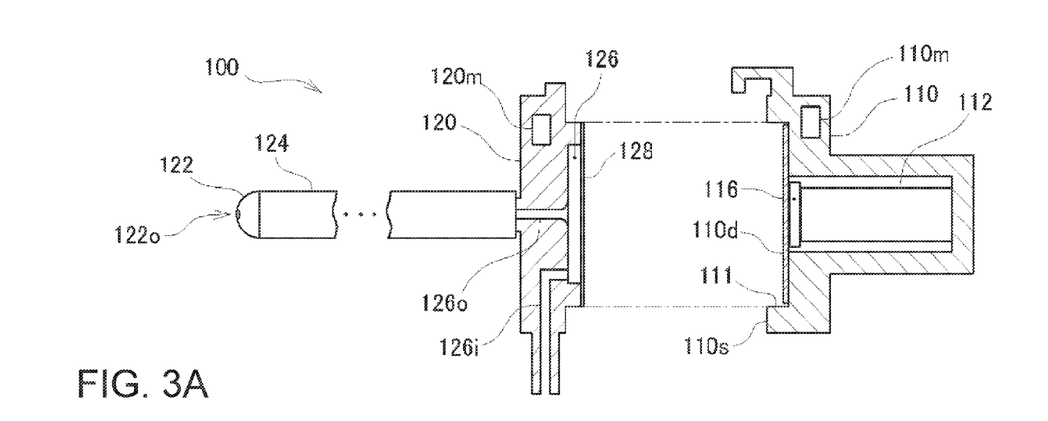
FIGS. 3A and 3B are sectional views showing the detailed configuration of the applicator.
Figure 3B:
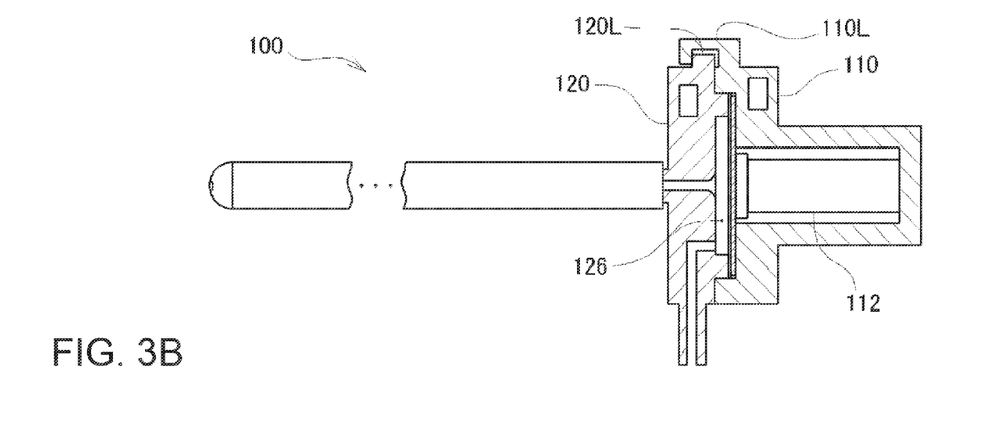

FIGS. 3A and 3B are sectional views showing the detailed configuration of the applicator 100. FIG. 3A shows the state where the distal end portion 120 is detached from the body portion 110. FIG. 3B shows the state where the distal end portion 120 is attached to the body portion 110. As shown in FIG. 3A, in the body portion 110, a shallow circular recessed part 111 is formed on the inner side of the joint surface 110s with the distal end portion 120 (see FIG. 2A) and a circular diaphragm 110d made of a thin metal plate is attached to a center position of the recessed part 111. On the back side of the diaphragm 110d, the piezoelectric element 112 is adhesively attached via a circular reinforcing plate 116. Also, a body-side memory 110m is arranged within the body portion 110. The body-side memory 110m is connected to the control unit 200 via wiring, not shown.

In the distal end portion 120, a shallow circular recessed shape is formed at a center position on the side to be joined with the body portion 110, and this recessed opening is covered with a highly elastic thin film 128 made of a silicone resin or the like, thus forming the liquid chamber 126. The liquid chamber 126 is connected to the second connection tube 304 via an inlet flow passage 126i and is also connected to the liquid injection pipe 124 via an outlet flow passage 126o. The nozzle 122 is attached to the distal end of the liquid injection pipe 124, and a liquid injection opening 122o for injecting the liquid is opened in the nozzle 122.

The part where the liquid chamber 126 is formed in the distal end portion 120 is formed as an inro-style fitting with the recessed part 111 of the body portion 110. As distal end portion 120 is attached to the body portion 110 and the male lock parts 120L are engaged with the female lock parts 110L, as shown in FIG. 3B, the thin film 128 of the liquid chamber 126 tightly contacts the diaphragm 110d of the body portion 110. Therefore, as a drive signal is applied to the piezoelectric element 112 in the state where the distal end portion 120 is attached to the body portion 110, the piezoelectric element 112 expands and thus deforms the thin film 128 via the reinforcing plate 116 and the diaphragm 110d. Consequently, the volume of the liquid chamber 126 is reduced and the liquid within the liquid chamber 126 is pressurized. The liquid is injected in a pulsed manner from the nozzle 122 via the outlet flow passage 126o and the liquid injection pipe 124.

Also, a distal end-side memory 120m is arranged within the distal end portion 120. As the distal end portion 120 is attached to the body portion 110, the distal end-side memory 120m is connected to the control unit 200 via wiring, not shown, and via the connection terminal 114 shown in FIG. 2A.

Figure 4:
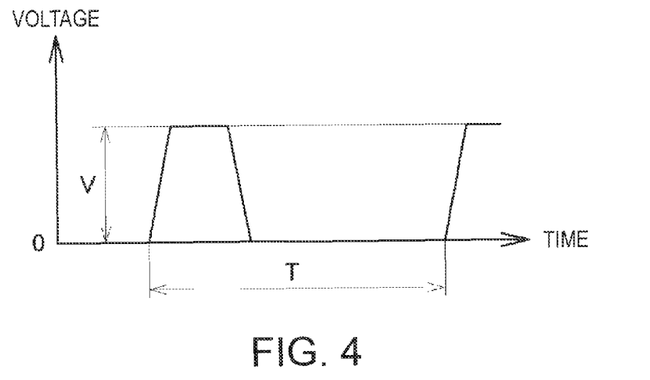
FIG. 4 is an explanatory view illustrating a drive signal applied to a piezoelectric element.

FIG. 4 is an explanatory view illustrating a drive signal applied to the piezoelectric element 112. The drive signal rises by a voltage V from an initial voltage (here, voltage 0) and then falls to the initial voltage again. As the applied voltage rises, the piezoelectric element 112 expands and thus reduces the volume of the liquid chamber 126. Here, the amount of expansion of the piezoelectric element 112 (hence the amount of volume reduction of the liquid chamber 126) is substantially proportional to the amount of rise of the applied voltage. Therefore, the liquid of a volume corresponding to the amount of voltage rise (here, voltage V) from the initial voltage is injected from the nozzle 122. Hereinafter, the amount of voltage rise (here, voltage V) from the initial voltage is referred to as a "drive voltage". In this embodiment, such a drive signal is applied to the piezoelectric element 112 on a predetermined cycle T. Hereinafter, the reciprocal number of the cycle T is referred to as a "drive frequency". The drive frequency represents the number of times of driving per second.

A-3. Configuration of Control Unit

Figure 5:
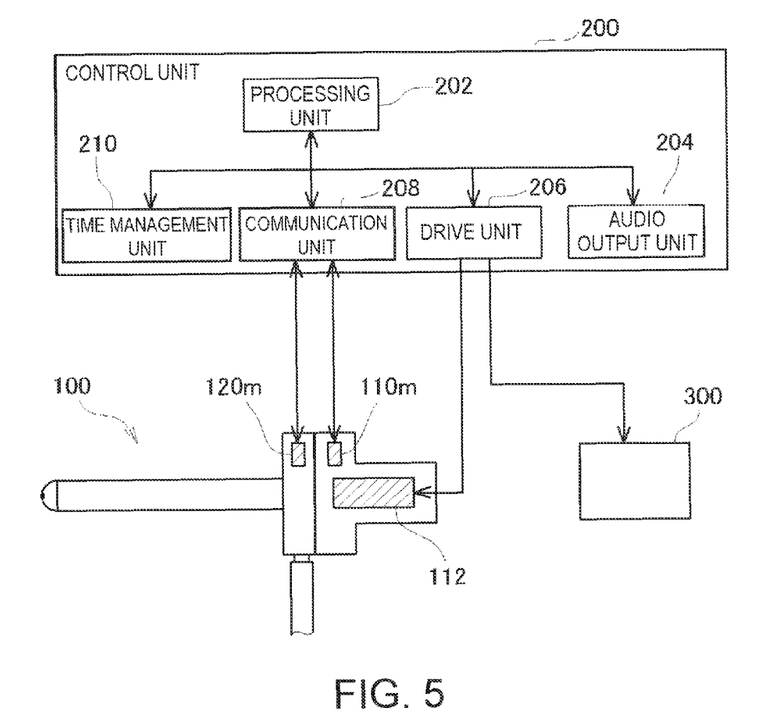
FIG. 5 is a block diagram showing the configuration of a control unit.

FIG. 5 is an explanatory view showing the schematic configuration of the control unit 200. In the control unit 200, a processing unit 202, an audio output unit 204, a drive unit 206, a communication unit 208, a time management unit 210 and the like are provided. The audio output unit 204 has a function of outputting a sound such as a buzz. The drive unit 206 outputs the drive signal shown in FIG. 4 to the piezoelectric element 112 of the applicator 100 and outputs a control signal to control the operation of the liquid supply instrument 300, to the liquid supply instrument 300. The communication unit 208 reads data from and writes data into the body-side memory 110m in the body portion 110 and the distal end-side memory 120m in the distal end portion 120. The time management unit 210 has a so-called timer function and a function of detecting the current time. Moreover, the processing unit 202 centrally controls the audio output unit 204, the drive unit 206, the communication unit 208 and the time management unit 210 and executes various kinds of processing for the liquid injection device 10 to operate properly.

As described above, in the liquid injection device 10 of this embodiment, the distal end portion 120, which is a portion through which the liquid passes in the applicator 100, is attachable to and removable from the body portion 110. Although various bacteria can grow in the portion through which the liquid passes if the liquid remains attached to this portion over a certain period of time after the use of the liquid injection device 10, the applicator 100 can be kept clean by replacing the distal end portion 120 alone. However, if the distal end portion 120 continues being used for a certain reason, for example, as the operator of the liquid injection device 10 forgets to replace the distal end portion 120, various bacteria can grow inside the applicator 100. Thus, in order to avoid such a situation, the following processing is carried out in the liquid injection device 10 of this embodiment.

B. Use Time Management Processing

Figure 6:
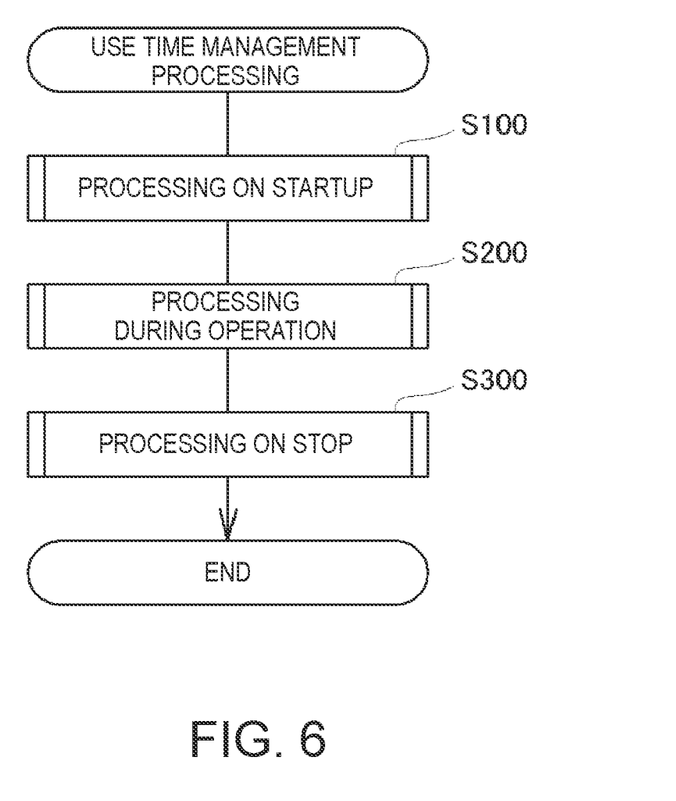
FIG. 6 is a flowchart showing use time management processing carried out by the control unit.

FIG. 6 is a flowchart of use time management processing executed by the processing unit 202 of the control unit 200 in order to manage the use time of the distal end portion 120. This processing is started as the operator of the liquid injection device 10 starts up the liquid injection device 10, and the processing is executed until the operation of the liquid injection device 10 ends. As the use time management processing is started, processing on startup (step S100) is executed first.

B-1. Processing on Startup

Figure 7:
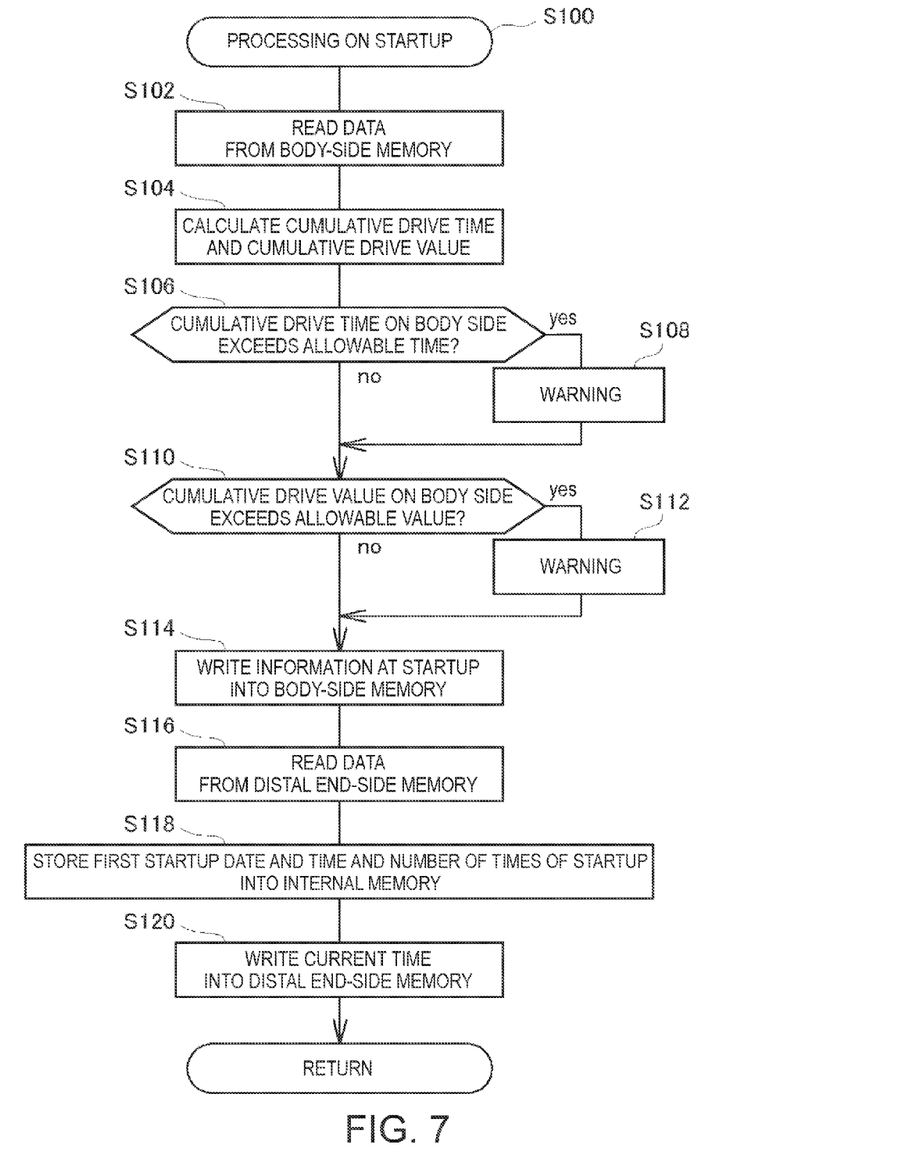
FIG. 7 is a flowchart showing processing on startup, carried out in the use time management processing.

FIG. 7 is a flowchart of the processing on startup, carried out by the processing unit 202 of the control unit 200 at the startup of the liquid injection device 10. In the processing on startup, various data stored in the body-side memory 110m are read out first (step S102).

Figure 8:
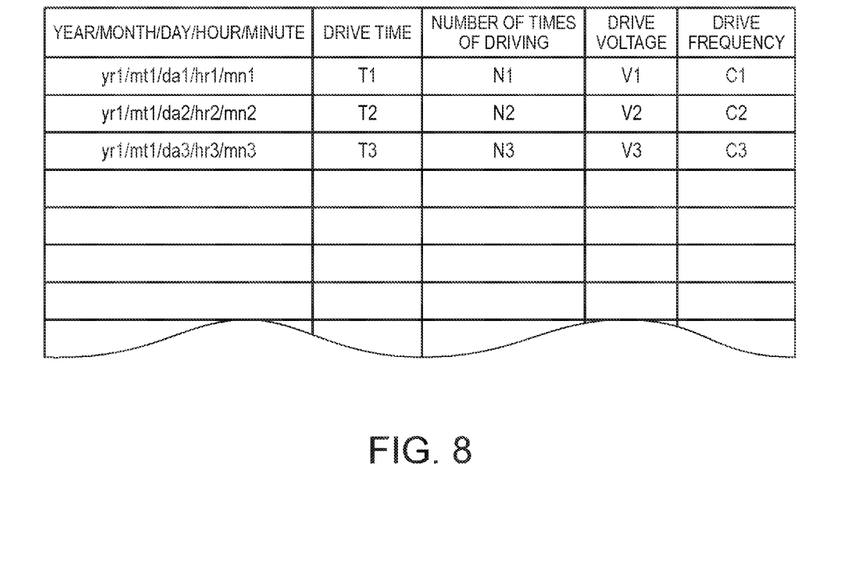
FIG. 8 is an explanatory view illustrating the way data is stored in a body-side memory.

FIG. 8 is an explanatory view showing the concept of the way various data are stored in the body-side memory 110m. In the liquid injection device 10 of this embodiment, data showing the year, month, day and time (year/month/day/hour/minute) of the date and time when the liquid injection device 10 is started up, and data such as the drive time, number of times of driving, drive voltage and drive frequency at that time are stored in the body-side memory 110m. Here, the drive time is the time during which the drive signal as shown in FIG. 4 is applied to drive the piezoelectric element 112. More simply, the time from the startup of the liquid injection device 10 until the liquid injection device 10 is stopped can be used as the drive time. The number of times of driving refers to the number of times the drive signal as shown in FIG. 4 is applied to the piezoelectric element 112 (in other words, the number of times the operation of the piezoelectric element 112 to expand and then return to the original length is repeated). The drive voltage is the voltage difference between an initial voltage and a maximum voltage of the drive signal. The drive frequency is the reciprocal number of the cycle T of the drive signal and shows the number of times the drive signal is applied per second (see FIG. 4).

In the example shown in FIG. 8, for example, the data on the top of the drawing shows that the liquid injection device 10 is started up for the first time at hour "hr1", minute "mn1" on day "da1", month "mt1", year "yr1", and that the drive time at that time is "T1", the number of times of driving is "N1", the drive voltage is "V1" and the drive frequency is "C1". Also, the liquid injection device 10 is started up twice after that, and the date and time of startup, the drive time, the number of times of driving, the drive voltage, the drive frequency or the like are stored for startup of each time. In step S102 of FIG. 7, these data stored in the body-side memory 110m are read out.

From the data shown in FIG. 8, it can be understood that the liquid injection device 10 is already started up three times. However, these data are stored in the body-side memory 110m arranged within the body portion 110 and therefore show the number of times the liquid injection device 10 is started up after the body portion 110 is loaded, to be more precise, rather than the number of times the liquid injection device 10 is started up.

After the data are readout from the body-side memory 110m, a cumulative drive time and a cumulative drive value of the body portion 110 are calculated (step S104). Here, the cumulative drive time is the total of the drive times in the past startup. For example, in the case of the data shown in FIG. 8, the drive time in the first startup is T1, the drive time in the second startup is T2, and the drive time in the third startup is T3. Therefore, the total of these "T1+T2+T3" is the cumulative drive time.

The cumulative drive value is the total of the numbers of times of driving, weighted according to the drive voltage in the past startup. In the case of the data shown in FIG. 8, the number of times of driving is N1 and the drive voltage is V1 in the first startup. In the second startup, the number of times of driving is N2 and the drive voltage is V2. In the third startup, the number of times of driving is N3 and the drive voltage is V3. Therefore, the total of a value K1×N1, which is, the first number of times of driving N1 multiplied by a weighting coefficient K1 corresponding to the drive voltage V1, a value K2×N2, which is, the second number of times of driving N2 multiplied by a weighting coefficient K2 corresponding to the drive voltage V2, and a value K3×N3, which is, the third number of times of driving N3 multiplied by a weighting coefficient K3 corresponding to the drive voltage V3, that is, the value "K1×N1+K2×N2+K3×N3" is the cumulative drive value.

Figure 9:
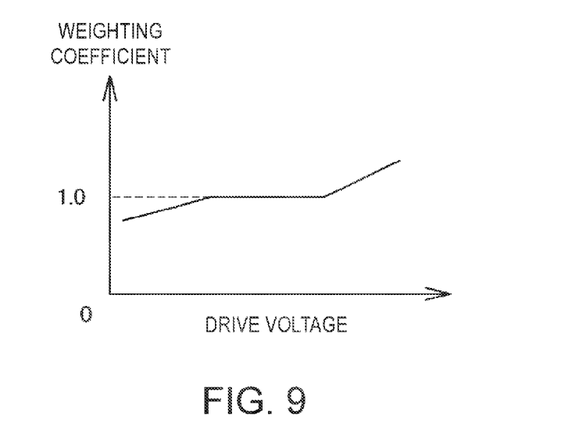
FIG. 9 is an explanatory view illustrating a weighting coefficient that is set according to the voltage of a drive signal.

FIG. 9 shows the way the weighting coefficient K is set according to the drive voltage. In a memory, not shown, arranged within the processing unit 202 of the control unit 200, the corresponding relation between the drive voltage and the weighting coefficient as shown in FIG. 9 is stored. The meaning of the weighting coefficient K that is set according to the drive voltage will be described later.

After the cumulative drive time and the cumulative drive value are thus calculated (step S104), whether the cumulative drive time exceeds a predetermined allowable time or not is determined (step S106). Here, the allowable time can be described as follows. As described with reference to FIGS. 3A and 3B, the applicator 100 injects the liquid by expanding the piezoelectric element 112 and thus reducing the volume of the liquid chamber 126. At this point, the diaphragm 110d of the body portion 110 repeats the operation of deforming as the piezoelectric element 112 expands and restoring the original shape as the piezoelectric element 112 contracts. Therefore, as the applicator 100 is used over a long period of time, the diaphragm 110d may be cracked or the diaphragm 110d may be less able to restore the original shape even when the piezoelectric element 112 contracts. Thus, an allowable time during which there is no risk of such situations is determined in advance for the body portion 110. In step S106 of FIG. 7, whether the cumulative drive time of the body portion 110 exceeds this allowable time or not is determined.

If the cumulative drive time exceeds the allowable time as a result of the determination (step S106: yes), the audio output unit 204 outputs a sound such as a predetermined buzz and thus issues a warning (step S108). Therefore, when a buzz is outputted at startup, the operator of the liquid injection device 10 can recognize that the use time of the body portion 110 of the applicator 100 exceeds the allowable time and that the body portion 110 needs to be replaced. As described above, since the allowable time is the time during which there is no risk of problems such as cracking of the diaphragm 110d of the body portion 110, the cumulative drive time exceeding the allowable time does not necessarily instrument that a problem immediately occurs with the body portion 110. Moreover, there may be some cases where a surgical operation must be carried out even though a new body portion 110 is not acquired yet for some reasons. Thus, the replacement of the body portion 110 is prompted simply by issuing a warning, instead of making the liquid injection device 10 unavailable for use, even if the cumulative drive time exceeds the allowable time (step S106: yes).

Meanwhile, if the cumulative drive time of the body portion 110 does not exceed the allowable time (step S106: no), whether the cumulative drive value that is previously calculated exceeds a predetermined allowable value or not is determined (step S110). Here, the allowable value is the following value. As described above, the diaphragm 110d of the body portion 110 repeats deformation every time the piezoelectric element 112 expands or contracts. Therefore, the time when problems occur such as a crack of the diaphragm 110d or the difficulty of the diaphragm 110d to restore the original shape is considered to be dependent on the number of times the diaphragm 110d is deformed (that is, the number of times the piezoelectric element 112 is driven). Also, it is considered that a crack or the like occurs sooner as the amount of each deformation (that is, the amount of deformation of piezoelectric element 112) is greater. Thus, an allowable value can be considered in such a way that problems do not occur if the cumulative value of the number of times the piezoelectric element 112 is driven, weighted according to the drive voltage and thus accumulated, does not exceed a certain value. The allowable value of the cumulative drive value is such a value. Also, the weighting coefficient K shown in FIG. 9 is a weighting coefficient added to the number of times of driving in consideration of the influence of the drive voltage when the number of times of driving is accumulated.

In step S110 of FIG. 7, whether the cumulative drive value of the body portion 110 exceeds this allowable value or not is determined. If the cumulative drive value exceeds the allowable value as a result of the determination (step S110: yes), the audio output unit 204 outputs a sound such as a predetermined buzz and thus issues a warning (step S112), as in the case where it is determined in step S106 that the cumulative drive time exceeds the allowable time. Consequently, the operator of the liquid injection device 10 can recognize that the body portion 110 of the applicator 100 needs to be replaced. The buzz that is outputted when the cumulative drive time exceeds the allowable time (step S106: yes) and the buzz that is outputted when the cumulative drive value exceeds the allowable value (step S110: yes) can be the same. Meanwhile, if the cumulative drive value does not exceed the allowable value (step S110: no), no warning is issued.

After the cumulative drive time and the cumulative drive value of the body portion 110 are calculated and a warning is issued when necessary, as described above (steps S104 to S112), information at the time of startup (information at startup) is written in the body-side memory 110m (step S114). Here, the information at startup is information such as the date and time when the liquid injection device 10 is started up and the drive voltage, drive frequency and the like of the drive signal applied to the piezoelectric element 112. The date and time when the liquid injection device 10 is started up can be acquired from the time management unit 210 included in the control unit 200. The drive voltage, drive frequency and the like are set by the operator when starting up the liquid injection device 10. Subsequently, the processing unit 202 of the control unit 200 this time reads out data stored in the distal end-side memory 120m of the distal end portion 120 (step S116).

Figure 10:
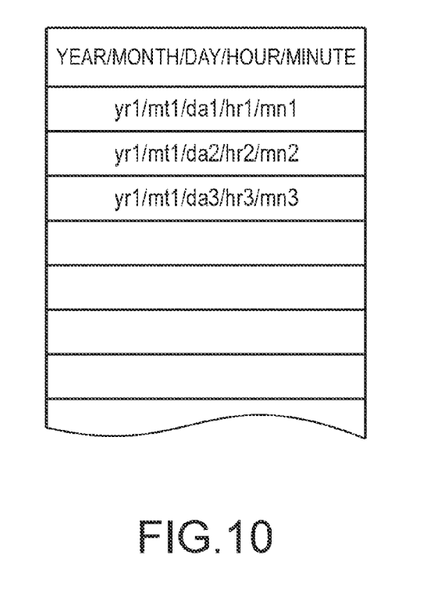
FIG. 10 is an explanatory view illustrating the way data is stored in a distal end-side memory.

FIG. 10 is an explanatory view showing the concept of the way data are stored in the distal end-side memory 120m. As shown in FIG. 10, the date and time when the distal end portion 120 is started up in the past (to be more precise, the date and time when the liquid injection device 10 is started up, with the distal end portion 120 loaded in the body portion 110) is stored in the distal end-side memory 120m. For example, in the example shown in FIG. 10, the current distal end portion 120 is started up for the first time at hour "hr1", minute "mn1" on day "da1", month "mt1", year "yr1", and subsequently started up twice (three times if the first time is included) Thus, the processing unit 202 of the control unit 200 stores the date and time of the first startup and the number of times the distal end portion 120 is started up already, into an internal memory, not shown, of the processing unit 202 (step S118). Then, the current date and time acquired from the time management unit 210 is additionally written into the distal end-side memory 120m. In the example shown in FIG. 10, the current date and time is written as the fourth startup date and time. After that, the processing on startup ends and returns to the use time management processing of FIG. 6.

In the above description, it is assumed that the date and time of startup of each time is stored in the distal end-side memory 120m. However, more simply, the date and time of the first startup and the number of times of startup in the past may be stored in the distal end-side memory 120m. In this case, the following processing is carried out in step S120 of FIG. 7. That is, if the date and time of the first startup is not stored in the distal end-side memory 120m, the current date and time is written as the date and time of the first startup. Meanwhile, if the date and time of the first startup is stored in the distal end-side memory 120m, the number of times of startup in the past stored in the distal end-side memory 120m is updated to a value that is greater by "1". For example, in the case of the second startup, the date and time of the first startup and the number of times of startup in the past (0) are stored in the distal end-side memory 120m. Thus, the date and time of the first startup is kept unchanged and the number of times of driving in the past is updated to a value (1) that is greater by 1.

Figure 11:
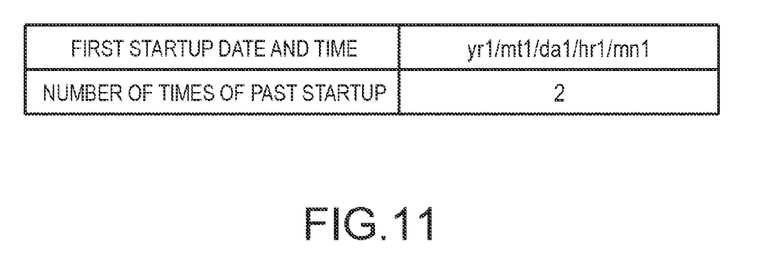
FIG. 11 is an explanatory view illustrating another example of the way data is stored in the distal end-side memory.

The data of the date and time of the first startup stored in the distal end-side memory 120m is equivalent to the "first startup data" according to the invention. In the case where the date and time of startup of each time is additionally written in the distal end-side memory 120m, as shown in FIG. 10, the number of startup dates and times stored in the distal end-side memory 120m expresses the number of times of startup. Therefore, in such a case, the data of the startup date and time stored in after the first time is equivalent to the "number of times of startup data" according to the invention. On the other hand, in the case where the number of times of startup in the past is stored instead of the date and time of startup of each time being additionally written in the distal end-side memory 120m, as shown in FIG. 11, the data of the number of times of startup in the past is equivalent to the "number of times of startup data" according to the invention.

B-2. Processing During Operation

Figure 12:
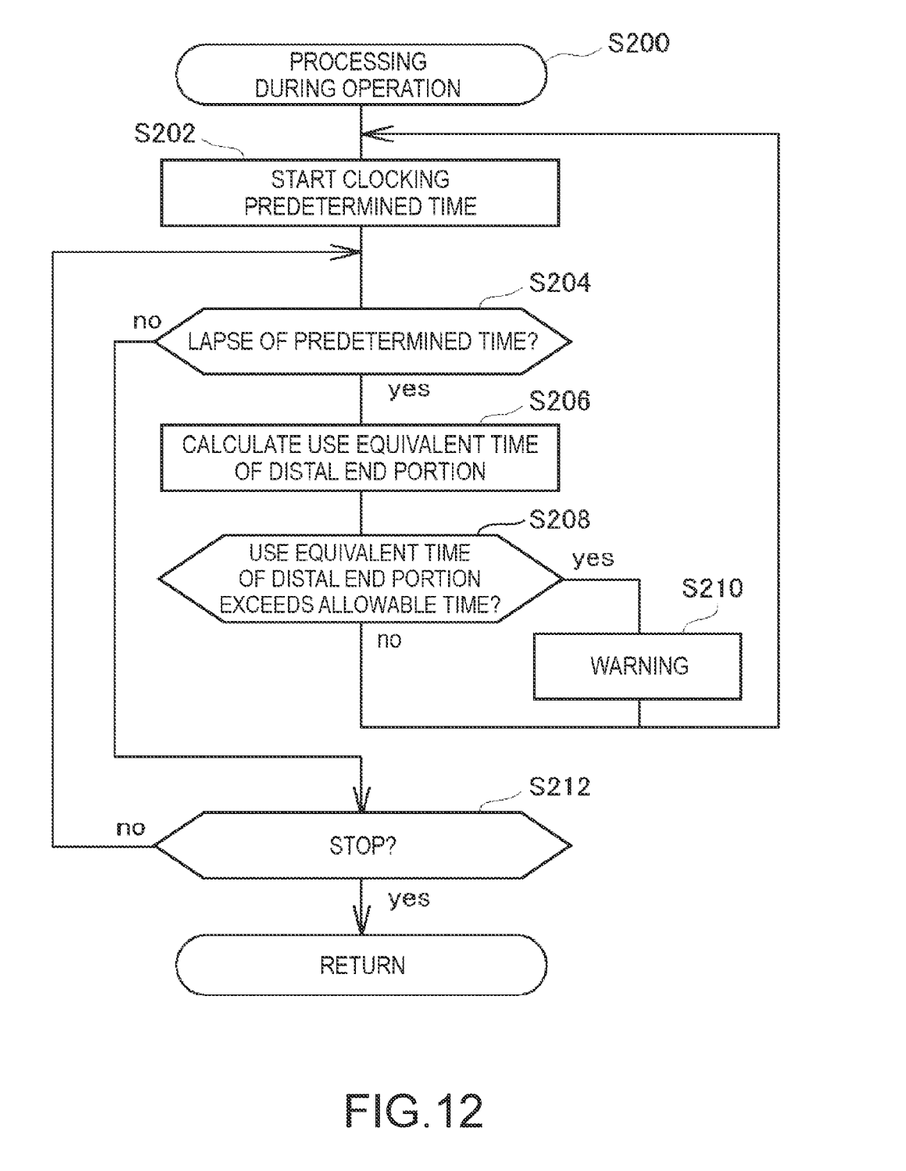
FIG. 12 is a flowchart showing processing during operation, carried out in the use time management processing.

FIG. 12 is a flowchart of the processing during operation carried out by the processing unit 202 of the control unit 200. This processing is the processing executed subsequently to the processing on startup (step S100) as shown in FIG. 6.

As the processing during operation (step S200) is started, the processing unit 202 first starts clocking a predetermined time, using the timer function of the time management unit 210 (step S202). Here, an arbitrary time can be set as the predetermined time by the operator of the liquid injection device 10. However, the predetermined time is typically 30 minutes or one hour. Next, whether there is already a lapse of the predetermined time that is set or not is determined (step S204). If there is not a lapse of the predetermined time yet (step S204: no), whether to stop the liquid injection device 10 or not, that is, whether a stop switch, not shown, provided on the liquid injection device 10 is operated by the operator or not, is determined (step S212). If the stop switch is not operated as a result of the determination (step S212: no), the processing returns to step S204 and whether there is already a lapse of the predetermined time or not is determined again.

If it is determined that there is a lapse of the predetermined time (step S204: yes) as such a determination is repeated, the processing unit 202 calculates a use equivalent time of the distal end portion 120 (step S206). Here, the use equivalent time of the distal end portion 120 refers to a time that is calculated based on the time elapsed since the distal end portion 120 is started up for the first time and in consideration of the number of times of startup in the past.

Figure 13A:
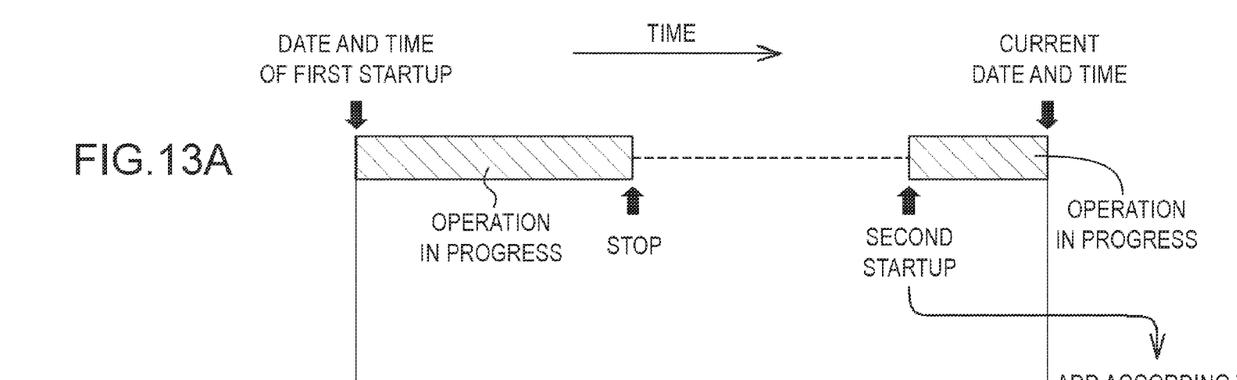
FIGS. 13A and 13B are explanatory views showing a method of calculating a use equivalent time of the distal end portion.
Figure 13B:
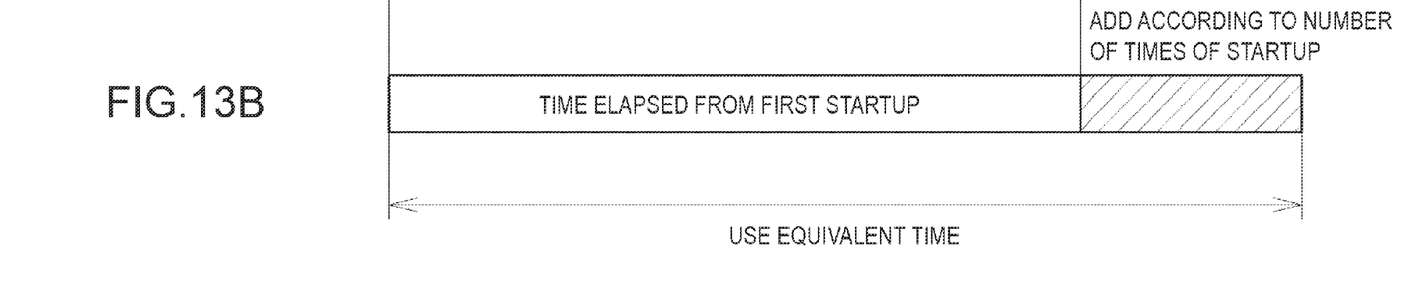

FIGS. 13A and 13B are explanatory views showing a method for calculating the use equivalent time of the distal end portion 120. FIG. 13A shows the state of use until now from when the distal end portion 120 is used for the first time. FIG. 13B shows the way the use equivalent time is calculated based on the state of use of the distal end portion 120. In the example shown in FIG. 13A, the distal end portion 120 is temporarily stopped after the first startup thereof, and after a while, the distal end portion 120 is started up again. In this case, at the current time, the operation based on the second startup is in progress. When calculating the use equivalent time, the processing unit 202 first calculates the time elapsed from the date and time of the first startup to the current date and time. The date and time of the first startup is read out from the distal end-side memory 120m in the foregoing processing on startup and stored in the internal memory of the processing unit 202 (step S118 of FIG. 7). The current date and time can be acquired from the time management unit 210.

Next, the number of times the distal end portion 120 is started up in the past (the number of times of startup in the past) is acquired. The number of times of startup in the past, too, is read out in the foregoing processing on startup and stored in the internal memory of the processing unit 202 (step S118 of FIG. 7). In the example shown in FIGS. 13A and 13B, since the operation based on the second startup is in progress at the current time, the number of times of startup in the past is 1. Then, for each time of the number of times of startup, a predetermined time (for example, four hours) is added to the time elapsed from the date and time of the first startup to the current date and time, and the resulting time is regarded as the use equivalent time (see FIG. 13B). In step S206 of FIG. 12, the use equivalent time of the distal end portion 120 is calculated in this manner.

Here, the use equivalent time has the following technical significance. First, the use equivalent time becomes longer as a longer time passes from the date and time of the first startup, and the use equivalent time also becomes longer as the number of times of startup in the past increases. Also, the risk of various bacteria growing inside the distal end portion 120 becomes higher as a longer time passes from the first use of the distal end portion 120. Moreover, the risk of various bacteria growing inside the distal end portion 120 becomes higher as the number of times the distal end portion 120 is reused increases. Therefore, it can be considered that the risk of various bacteria growing inside the distal end portion 120 becomes higher as the use equivalent time becomes longer.

Thus, whether the calculated use equivalent time exceeds a preset allowable time of the distal end portion 120 or not is determined (step S208). If the use equivalent time exceeds the allowable time as a result of the determination (step S208: yes), the audio output unit 204 outputs a sound such as a predetermined buzz and thus issues a warning (step S210). On the other hand, if the use equivalent time does not exceed the allowable time (step S208: no), no warning is issued and the processing returns to step S202 to start clocking a predetermined time.

As is clear from the above description, the use equivalent time is used as an indicator indicating the risk of various bacteria growing inside the distal end portion 120. Therefore, the weight on the time elapsed from the date and time of the first startup and the number of times of startup in the past can be properly changed in such a way that the use equivalent time serves as a more appropriate indicator. For example, in the calculation, the time elapsed from the date and time of the first startup may be halved, or a longer time (for example, ten hours) for each time of the number of times of startup in the past may be adopted.

Also, it is desirable that the buzz that is outputted when the use equivalent time of the distal end portion 120 exceeds the allowable time is different from the buzz that is outputted when the cumulative drive time of the body portion 110 exceeds the allowable time or when the cumulative drive value exceeds the allowable value. Thus, simply by hearing the buzz, the operator of the liquid injection device 10 can recognize that the distal end portion 120 of the applicator 100 needs to be replaced.

In this way, in the processing during operation, the operation of calculating the use equivalent time every time a predetermined time passes (step S206) and warning the operator to replace the distal end portion 120 (step S210) if the resulting use equivalent time reaches the allowable time (step S208: yes), are repeated until the operator stops the liquid injection device 10. Then, as the operator operates the stop switch on the liquid injection device 10 (step S212: yes), the processing during operation ends and returns to the use time management processing of FIG. 6. After that, the following processing on stop (step S300) starts.

B-3. Processing on Stop

Figure 14:
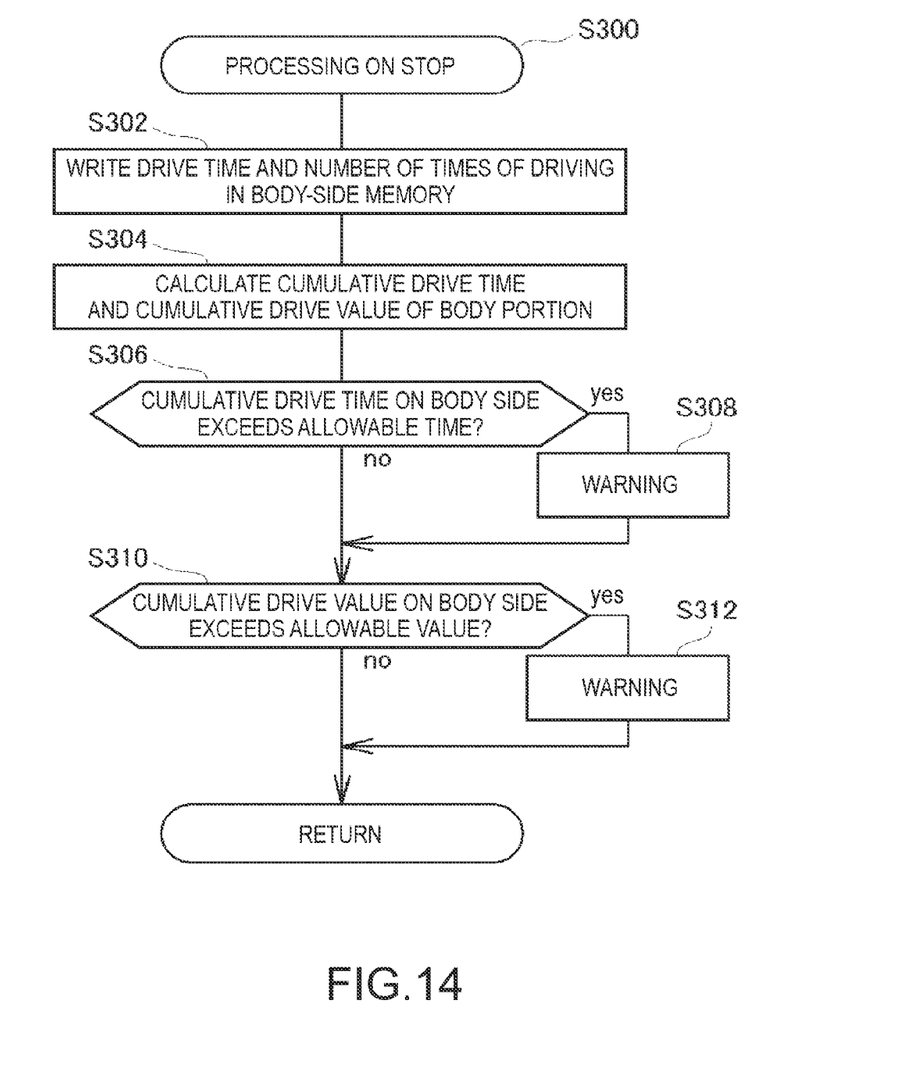
FIG. 14 is a flowchart showing processing on stop, carried out in the use time management processing.

FIG. 14 is a flowchart of the processing on stop, carried out by the processing unit 202 of the control unit 200. In the processing on stop, the drive time for which the piezoelectric element 112 is driven and the number of times the piezoelectric element 112 is driven during the period from the startup to the stop of this time are written into the body-side memory 110m (step S302). That is, in step S114 of the processing on startup described with reference to FIG. 7, the date and time of startup and the information at startup such as drive voltage and drive frequency are written in the body-side memory 110m, but the drive time and the number of times of driving at the startup point are not known and therefore not written. Thus, when the liquid injection device 10 is stopped, processing to write the finalized drive time and number of times of driving into the body-side memory 110m is carried out. In this way, of the data shown in FIG. 8 stored in the body-side memory 110m, the date and time of startup, drive voltage, drive frequency and the like are written when the liquid injection device 10 is started up, and the drive time, number of times of driving and the like are written when the liquid injection device 10 is stopped. The drive voltage written into the body-side memory 110m when the liquid injection device 10 is stopped is equivalent to the "drive time data" according to the invention, and the number of times of driving is equivalent to the "number of times of driving data" according to the invention.

Next, the processing unit 202 of the control unit 200 calculates the cumulative drive time and the cumulative drive value of the body portion 110 as of the present time, using the data that are already stored in the body-side memory 110m and the data that are newly written in the body-side memory 110m (step S304). The method of calculating the cumulative drive time and the cumulative drive value is similar to the method of calculation in step S104 of the processing on startup.

Then, whether the calculated cumulative drive time exceeds an allowable time or not is determined (step S306). If the cumulative drive time exceeds the allowable time (step S306: yes), the audio output unit 204 outputs a buzz or the like to issue a warning (step S308). Also, whether the calculated cumulative drive value exceeds an allowable value or not is determined (step S310) and if the cumulative drive value exceeds the allowable value (step S310: yes), the audio output unit 204 outputs a buzz or the like to issue a warning (step S312). Meanwhile, if the newly calculated cumulative drive time does not exceed the allowable time (step S306: no) and the newly calculated cumulative drive value does not exceed the allowable value, either (step S310: no), the processing on stop of FIG. 14 ends without issuing a warning and returns to the use time management processing of FIG. 6. After that, the use time management processing ends, too.

As described above in detail, in the liquid injection device 10 of this embodiment, the distal end-side memory 120m is loaded in the distal end portion 120 of the applicator 100. The date and time when the distal end portion 120 is used for the first time (the date and time of first startup) and the number of times of use in the past (number of times of startup) are stored in the distal end-side memory 120m. After the liquid injection device 10 is started up, the use equivalent time of the distal end portion 120 is calculated based on the data stored in the distal end-side memory 120m and the current time. If the resulting time exceeds an allowable time, a warning to prompt replacement of the distal end portion 120 is issued every predetermined time period. Therefore, the risk of various bacteria growing inside the distal end portion 120 as the operator of the liquid injection device 10 forgets to replace the distal end portion 120 can be avoided.

Also, the body-side memory 110m is loaded in the body portion 110 of the applicator 100. The data of the drive time, drive voltage, number of times of driving and the like of the piezoelectric element 112 are stored in the body-side memory 110m. When the liquid injection device 10 is started up or stopped, the cumulative drive time and the cumulative drive value of the body portion 110 are calculated based on these data. If the cumulative drive time exceeds an allowable time, or if the cumulative drive value exceeds an allowable value, a warning to prompt replacement of the body portion 110 is issued. Situations such as cracking of the diaphragm 110d of the body portion 110 while the liquid injection device 10 is in use can be avoided in advance. In addition to the drive time, drive voltage, number of times of driving and the like of the piezoelectric element 112, the date and time of startup of the liquid injection device 10 and the data about the drive frequency of the piezoelectric element 112 are stored in the body-side memory 110m. Therefore, even when a certain problem occurs while the liquid injection device 10 is in use, the cause of the problem can be specified by checking these data stored in the body-side memory 110m.

The liquid injection device according to the invention is described above, using an exemplary embodiment. However, the invention is not limited to the embodiment and can be carried out in various forms without departing from the scope of the invention.

For example, in the processing on startup (step S100 and the processing on stop (step S300) in the use time management processing, a warning to replace the body portion 110 may be issued. When a warning is issued, the fact that the warning is issued or the date and time when the warning is issued may be stored in the body-side memory 110m. Similarly, in the processing during operation (step S200), a warning to replace the distal end portion 120 may be issued. When a warning is issued, the fact that the warning is issued or the date and time when the warning is issued may be stored in the distal end-side memory 120*m*.

This application claims priority to Japanese Patent Application No. 2011-227662, filed on Oct. 17, 2011, the entirety of which is hereby incorporated by reference.

What is claimed is:

1. A liquid injection device comprising:
   an injection unit which injects a liquid;
   a liquid supply instrument which supplies the liquid to the injection unit; and
   a control unit which controls operation of the injection unit and the liquid supply instrument,
   wherein the injection unit includes
      a distal end portion where a nozzle for injecting the liquid is formed, and
      a body portion in which the distal end portion is removably loaded,
   at the distal end portion, a distal end-side memory is provided in which first startup data, which is data related to date and time when the liquid injection device is started up for the first time as the distal end portion is loaded in the body portion, is written, and
   the control unit is a control unit which reads and writes the first startup data from and to the distal end-side memory in the distal end portion loaded in the body portion and manages use time of the distal end portion based on the first startup data that is read out.

2. The liquid injection device according to claim 1, wherein number of times of startup data, which is data related to the number of times the liquid injection device is started up as the distal end portion is loaded, is written in the distal end-side memory, in addition to the first startup data, and
   the control unit reads and writes the first startup data and the number of times of startup data from and to the distal end-side memory of the distal end portion and manages the use time of the distal end portion based on the first startup data and the number of times of startup data that are read out.

3. The liquid injection device according to claim 1, wherein the distal end portion includes a liquid chamber to which the liquid is supplied from the liquid supply instrument and which is connected to the nozzle,
   the body portion includes
      a piezoelectric element which deforms according to a voltage of an applied drive signal and changes a volume of the liquid chamber, and
      a body-side memory in which drive time data, which is data related to a drive time during which the drive signal is applied to the piezoelectric element, is written, and
   the control unit is a control unit which
      applies the drive signal which reduces the volume of the liquid chamber to the piezoelectric element,
      reads and writes the drive time data from and to the body-side memory, and
      manages use time of the body portion based on the drive time data read out from the body-side memory.

4. The liquid injection device according to claim 1, wherein the distal end portion includes a liquid chamber to which the liquid is supplied from the liquid supply instrument and which is connected to the nozzle,
   the body portion includes
      a piezoelectric element which deforms according to a voltage of an applied drive signal and changes a volume of the liquid chamber, and
      a body-side memory in which number of times of driving data, which is data related to the number of times the drive signal is applied to the piezoelectric element, is written, and
   the control unit is a control unit which
      applies the drive signal which reduces the volume of the liquid chamber to the piezoelectric element,
      reads and writes the number of times of driving data from and to the body-side memory, and
      manages use time of the body portion based on the number of times of driving data read out from the body-side memory.

5. The liquid injection device according to claim 4, wherein the number of times of driving data is data related to the number of times of driving and the voltage of the drive signal.

6. A medical apparatus comprising the liquid injection device according to claim 1.

7. A medical apparatus comprising the liquid injection device according to claim 2.

8. A medical apparatus comprising the liquid injection device according to claim 3.

9. A medical apparatus comprising the liquid injection device according to claim 4.

10. A medical apparatus comprising the liquid injection device according to claim 5.

* * * * *